United States Patent
Tiefenbrun et al.

(10) Patent No.: US 6,331,182 B1
(45) Date of Patent: Dec. 18, 2001

(54) MEDICAL TWISTING DEVICE AND METHOD FOR FORMING A SURGICAL CLOSURE

(76) Inventors: Jonathan Tiefenbrun, 62 Country Rd., Marmaroneck, NY (US) 10543; Peter J. Wilk, 185 West End Ave., New York, NY (US) 10023

(*) Notice: Subject to any disclaimer, the term of this patent is extended or adjusted under 35 U.S.C. 154(b) by 0 days.

(21) Appl. No.: 09/459,437
(22) Filed: Dec. 13, 1999
(51) Int. Cl.⁷ .................................................. A61B 17/04
(52) U.S. Cl. ......................... 606/144; 606/146; 606/148
(58) Field of Search ................................... 606/144–148, 606/139

(56) References Cited

U.S. PATENT DOCUMENTS

| | | | |
|---|---|---|---|
| 4,935,027 | * | 6/1990 | Yoon ..................................... 606/146 |
| 5,501,690 | * | 3/1996 | Measamer et al. ................... 606/146 |
| 5,797,927 | * | 8/1998 | Yoon ..................................... 606/144 |
| 6,096,051 | * | 8/2000 | Kortenbach et al. ................ 606/144 |

FOREIGN PATENT DOCUMENTS

WO 2000 12013 * 8/1999 (WO) ............................ A61B/17/04

* cited by examiner

Primary Examiner—Gary Jackson
(74) Attorney, Agent, or Firm—R. Neil Sudol; Henry E. Coleman; William J. Sapone

(57) ABSTRACT

A procedure wherein an elongate, at least partially flexible tie member is partially wound about tissues to be closed at a surgical site. Opposite ends of the flexible tie element are entrained by a twisting instrument which has a distal end juxtaposed to the surgical site. The twisting instrument extends out of the patient so that a proximal end of the instrument is manipulable by a surgeon. The surgeon rotates the instrument about a longitudinal axis, thereby twisting the tie member multiple turns about itself. Where the tie member is a wire, the twisting effectively locks the tie member at the surgical site. The tie member may then be severed by a cutters so that the tissues are closed.

17 Claims, 5 Drawing Sheets

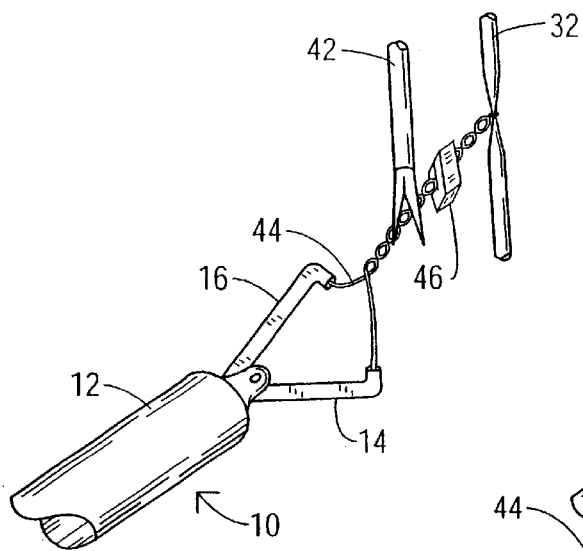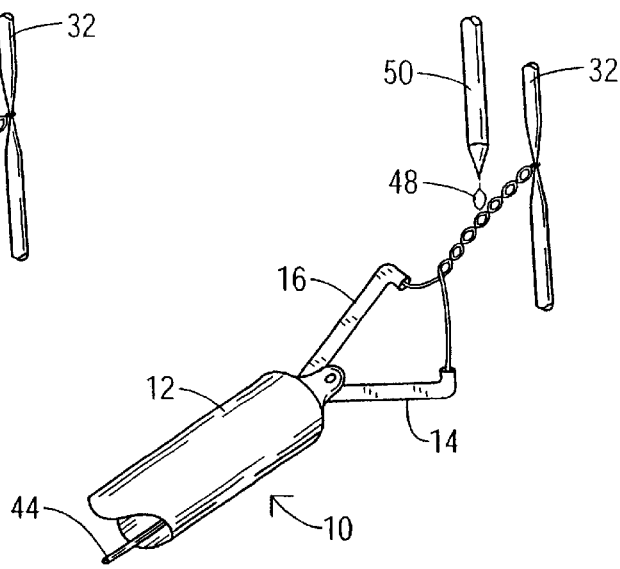
FIG. 4    FIG. 5
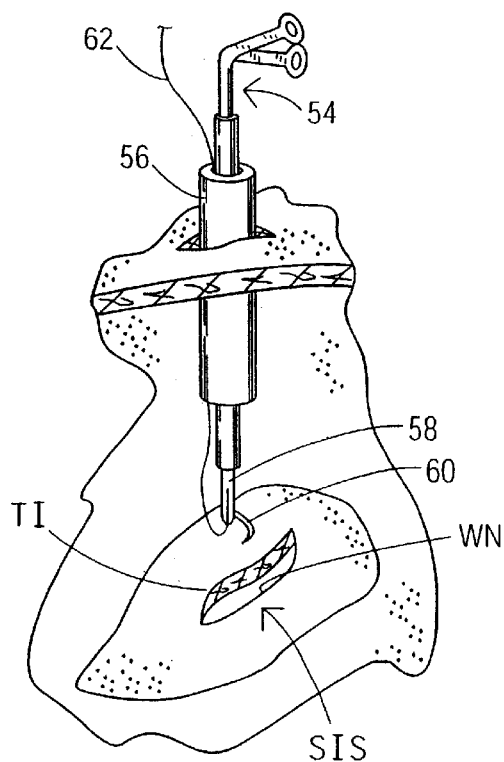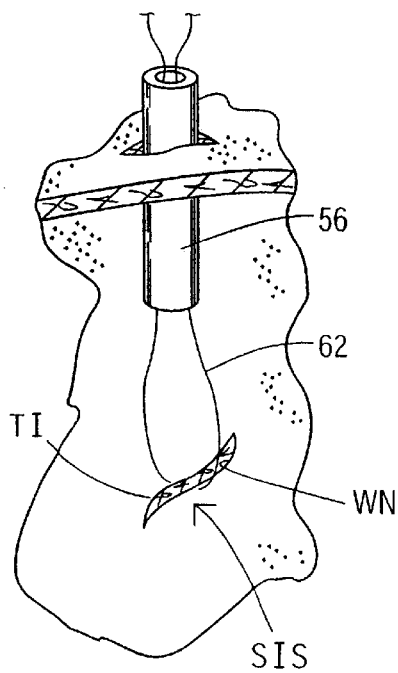
FIG. 6A    FIG. 6B

MEDICAL TWISTING DEVICE AND METHOD FOR FORMING A SURGICAL CLOSURE

BACKGROUND OF THE INVENTION

This invention relates to a method for forming a surgical closure. This invention also relates to a device for use in the method. More specifically, this invention relates to a surgical instrument and an associated method for forming a closure in organic tissues of a patient in a minimally invasive endoscopic operation. The invention is useful in laparoscopic, arthroscopic, thoracoscopic, etc., procedures.

Minimally invasive surgical procedures such as laparoscopy, arthroscopy, thoracoscopy, etc., use endoscopes (laparoscopes, arthroscopes . . .) for enabling visual observation of a surgical site below the patient's skin surface. These minimally invasive operations generally entail the placement of one or more cannulas in the patient's skin. The cannulas penetrate to the surgical site and various instruments are inserted through the cannulas to perform an operation on organic tissues which remain mostly covered by the skin surfaces of the patient.

A continuing problem in such minimally invasive operations is the formation of surgical closures inside the body. The suturing of an incision, the closure of a wound or the ligating of a tube inside the body through endoscopic cannulas is a difficult and tedious task. Various methods have been proposed for simplifying and facilitating the formation of sutures. U.S. Pat. No. 5,037,433, for example, discloses a method for performing a surgical operation on internal body tissues of a patient which comprises the steps of inserting a tubular endoscope member through an aperture in the patient's body, using the endoscope to visually locate the internal body tissues inside the patient's body, and upon locating the surgical site, pushing an elongate flexible rod member in a distal direction through a biopsy channel in the tubular endoscope member to eject a needle disposed in a straightened configuration inside the channel at a distal end of the tubular endoscope member. In this method, the needle has a spring bias construction tending to automatically bend the needle into an arcuate configuration, and the needle further has a proximal end attached to a suture. Upon ejection of the needle from the endoscope biopsy channel, the needle is passed in the arcuate configuration through the internal body tissues. After passing of the needle through the internal body tissues, the suture is closed, whereupon the tubular endoscope member is withdrawn or removed from the patient's body though the introduction aperture.

Other recently proposed methods entail the tying of sutures outside the body and sliding the suture ties down through a cannula to the surgical site inside the patient.

Nevertheless, despite these recent proposals, no method has been generally adopted by surgeons who regularly perform minimally invasive surgical operations.

OBJECTS OF THE INVENTION

An object of the present invention is to provide an instrument and/or an associated method for forming a surgical closure inside a patient through a small opening in the skin surface of the patient.

Another object of the present invention is to provide such an instrument and associated closure method which is easy to use.

A further object of the present invention is to provide such an instrument and associated method which result in a reliable closure.

These and other objects of the present invention will be apparent from the drawings and descriptions herein.

SUMMARY OF THE INVENTION

These objects are attained in a procedure wherein an elongate, at least partially flexible tie member is partially wound about tissues to be closed at a surgical site. Opposite ends of the flexible tie element are entrained by a twisting instrument which has a distal end juxtaposed to the surgical site. The twisting instrument extends out of the patient so that a proximal end of the instrument is manipulable by a surgeon. The surgeon rotates the instrument about a longitudinal axis, thereby twisting the tie member multiple turns about itself.

Where the tie member is a wire, the twisting effectively locks the tie member at the surgical site. The tie member may then be severed by a cutters so that the tissues are closed.

Where the tie member is a suture, the suture may be locked after the twisting operation by placing a clamp or clip on the twisted portion of the suture. The clamp or clip may be a welded clip as disclosed in U.S. Pat. No. 5,383,883, the disclosure of which is hereby incorporated by reference. The locking of the suture may additionally or alternatively be effectuated through the application of glue. A glue gun or ejector may be used to apply a drop of glue to the twisted part of the suture prior to the severing of the suture. Alternatively, the glue may be dried on the suture and subsequently activated by a heating instrument.

In one embodiment of the present invention, the twisting instrument has a pair of pivoting jaws at a distal end. The jaws are provided with a passageway for the tie member. The instrument is inserted into the patient and the jaws opened and subsequently closed about the tissues (e.g., a blood vessel or duct). After the closure of the jaws inside the patient, an end of the tie member is threaded from one jaw to another and gripped by the second jaw. The jaws are then opened and pulled away from the surgical site. The tie member slides out of the first jaw during the opening of the jaws and during the withdrawal of the instrument from the surgical site. Thus, a loop is formed about the tissues to be closed. The instrument is then turned about its longitudinal axis, thereby twisting the tie member between the jaws and the target tissues of the patient. Where the tie member is a wire, the twisting effectively locks the tie member at the surgical site. Where the tie member is a suture, the suture is locked after the twisting operation by an additional procedural step such as placing a clamp or clip and/or gluing. After locking, the tie member is severed by a cutters so that the tissues are closed.

Other types of twisting devices may be used to perform a surgical closure operation in accordance with the present invention. For example, an elongate tube provided at a distal end with a pair of eyelets, or a pair of hooks, may be used for twisting a wire or suture after the wire or suture has been partially wound around tissues to be closed. This winding can be accomplished with elongate forceps-type instruments commonly used in minimally invasive endoscopic operations.

BRIEF DESCRIPTION OF THE DRAWINGS

FIG. 4 is a schematic perspective view, similar to FIG. 3E, showing an alternative step in the laparoscopic operation illustrated in FIGS. 2 and 3A–3F.

FIG. 5 is a schematic perspective view, similar to FIG. 3E, showing another alternative step in the laparoscopic operation illustrated in FIGS. 2 and 3A–3F.

FIGS. 6A–6D are schematic sectional views of a patient undergoing a laparoscopic closure operation in accordance with the present invention, utilizing a different instrument.

DESCRIPTION OF THE PREFERRED EMBODIMENTS

Figure 1:
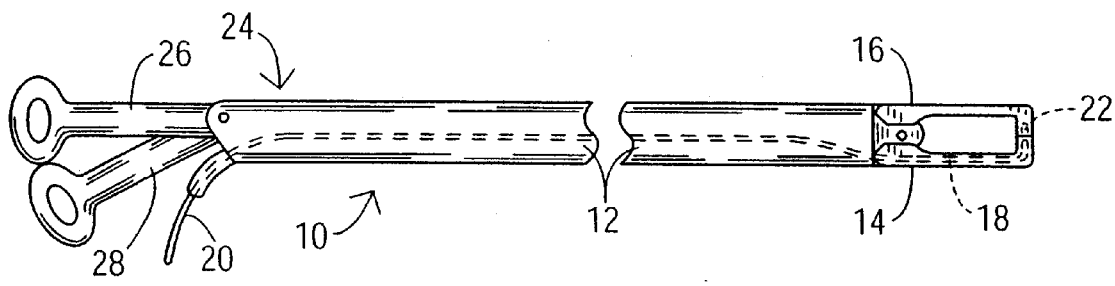
FIG. 1 is a schematic side elevational view of a laparoscopic or arthroscopic instrument in accordance with the present invention.

As illustrated in FIG. 1, a surgical instrument 10 for use in performing surgical closures in minimally invasive endoscopic-type procedures such as laparoscopic or arthroscopic surgery includes an elongate shaft 12 provided at a distal end with a pair of pivotably mounted jaws 14 and 16. At least one jaw 14 is provided with a passageway 18 through which extends an at least partially flexible tie member 20 such as a wire. The other jaw 16 is provided with an opening 22 which serves to grip a free end of wire 20 upon a pushing of wire 20 through passageway 18. The gripping action may be accomplished by a friction fit of wire 20 in opening 22. Alternatively, jaw 16 may be provided with an active gripping element such as a clamp actuatable from a proximal end 24 of instrument 10. A pair of pivotably mounted handgrips 26 and 28 extending from proximal end 24 of instrument 10 are operatively coupled to jaws 14 and 16 for alternately opening and closing the jaws.

Figure 2:
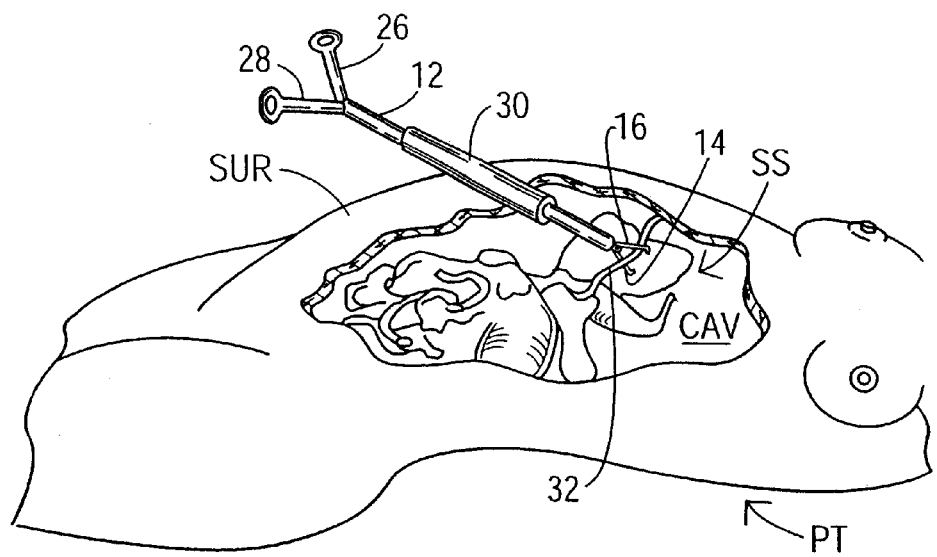
FIG. 2 is a partial schematic view, partially broken away, of a patient undergoing a laparoscopic closure operation utilizing the instrument of FIG. 1.

As illustrated in FIG. 2, instrument 10 is inserted into a patient PT through a cannula 30 which traverses a skin surface SUR of the patient and extends into a natural or artificially generated cavity CAV to a surgical site SS. Upon insertion of a distal end portion of instrument 10 through cannula 30, handgrips 26 and 28 are actuated to open jaws 14 and 16, as shown in FIG. 2. Further steps in the laparoscopic procedure are depicted in FIGS. 3A–3F. First, handgrips 26 and 28 are operated to close jaws 14 and 16 about tissues 32 to be closed. In the example of FIGS. 2 and 3A–3F, these tissues 32 take the form of a tube (e.g., a cystic duct) or a blood vessel.

Upon the closure of jaws 14 and 16, closure wire 20 is pushed through passageway 18 and into opening 22, whereupon the free or distal end of wire 20 is gripped by jaw 16. In the event that a suture rather than wire 20 is used as the closure or tie member, jaw 16 is provided with a gripper, such as clamping jaws (not illustrated). This gripper is attached to a tensile element or rod (not shown) which extends back to the proximal end of instrument 10. The tensile element or rod is pulled to draw the free end of the suture out of jaw 14 and into jaw 16.

Figure 3A:
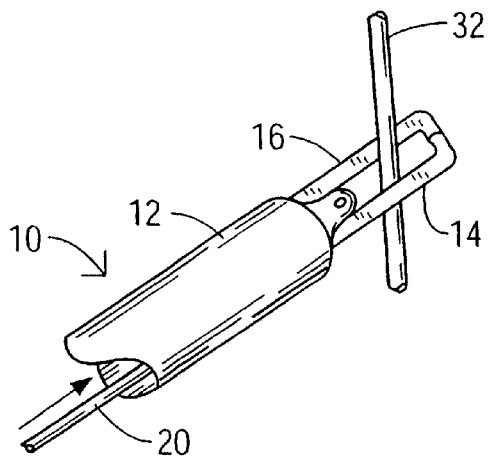
FIGS. 3A–3F are respective schematic perspective views showing additional successive steps in the operation depicted in FIG. 2.
Figure 3B:
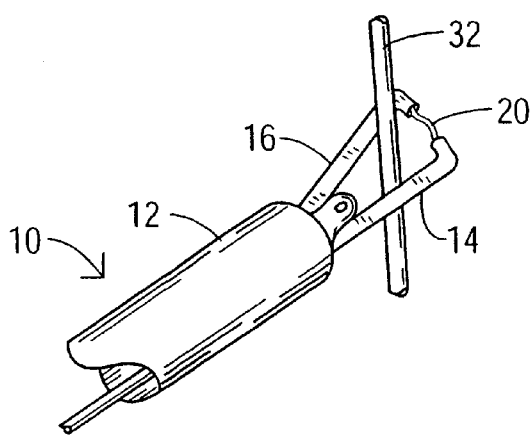
Figure 3C:
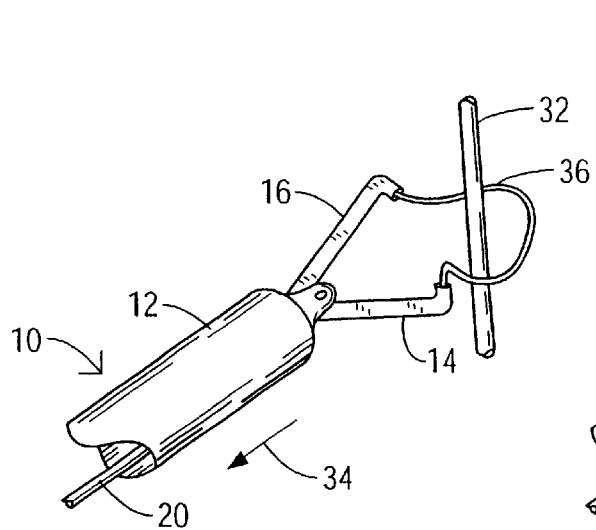
Figure 3D:
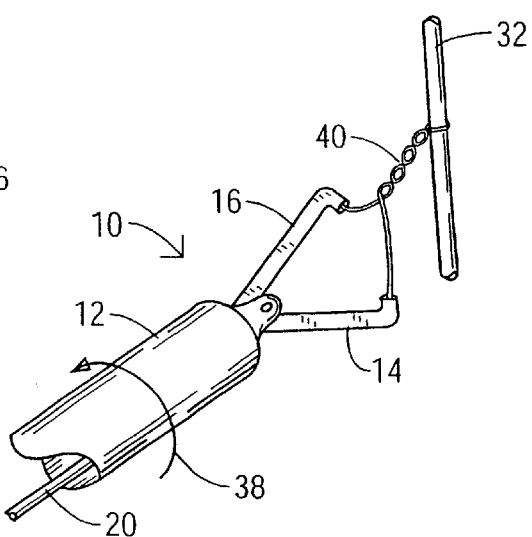

After the extension of closure or tie wire 20 from jaw 14 to jaw 16, handgrips 26 and 28 are again actuated to open jaws 14 and 16, as illustrated in FIG. 3B. At that juncture, the entire instrument 10 is drawn in a proximal direction, as indicated by an arrow 34 in FIG. 3C, so that a loop 36 is formed in wire 20, the loop being partially wound about tube or duct 32. Upon the formation of loop 36, instrument 10 is rotated about its longitudinal axis, as indicated by an arrow 38 in FIG. 3D. This rotation twists closure or tie wire 20 about itself, as indicated at 40.

Figure 3E:
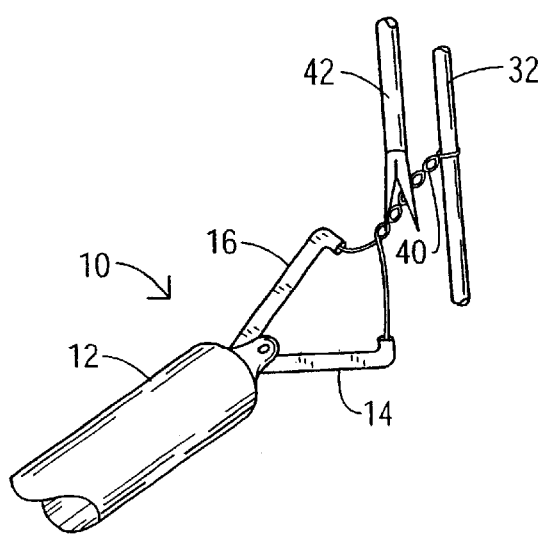
Figure 3F:
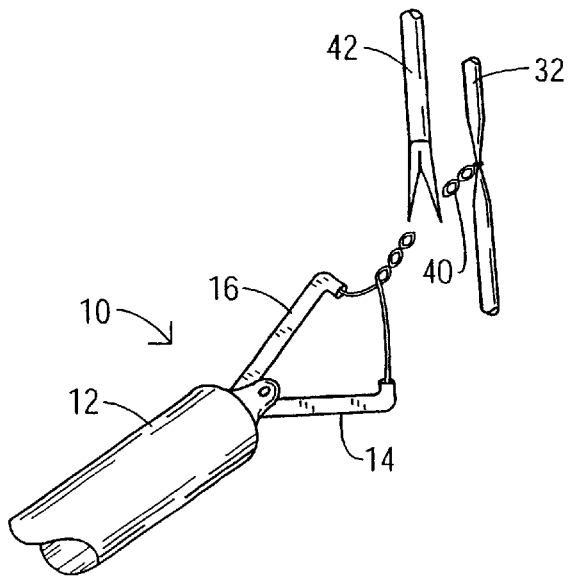

As illustrated in FIG. 3E, a laparoscopic scissors or clipper instrument 42 is inserted into the patient's cavity CAV via another laparoscopic trocar sleeve or cannula (not shown). After the formation of twists 40 in wire 20, scissors or clipper instrument 42 is operated to sever the wire 20 (FIG. 3F). Twists 40 are permanent deformations of wire 20 and serve to lock the wire in a closure about tube or duct 32.

FIG. 4 shows a variation of the operation of FIGS. 2 and 3A–3F where a suture 44 is used instead of a wire 20 to close tube or duct 32. A clip or clamp 46 made of biocompatible material is placed about suture 44 to lock the suture after a twisting thereof pursuant to the step shown in FIG. 3D. Clip or clamp 46 may closed or locked by ultrasonic welding or convention heating, as disclosed in U.S. Pat. No. 5,383,883, the disclosure of which is hereby incorporated by reference. Other types of clips are also possible, including, for instance, hook and loop type fastening elements.

FIG. 5 depicts an alternative locking technique to the procedure of FIG. 4 where suture 44 is used to close tube or duct 32. Instead of or in addition to clip 46, a drop of biocompatible adhesive 48 is applied to the twisted suture via a laparoscopic or arthroscopic glue gun 50. After glue drop 48 dries, scissors or clipper instrument 42 is used to sever the suture on a side of the dried glue drop 48 opposite tube or duct 32.

In an alternative non-illustrated procedure, the suture is coated with a layer of glue which can be activated or set by the application of heat, radiation, ultrasonic vibrations, or other form of energy,. An instrument applies the energy after the twisting of the suture at the surgical site as described above or below.

Figure 6C:
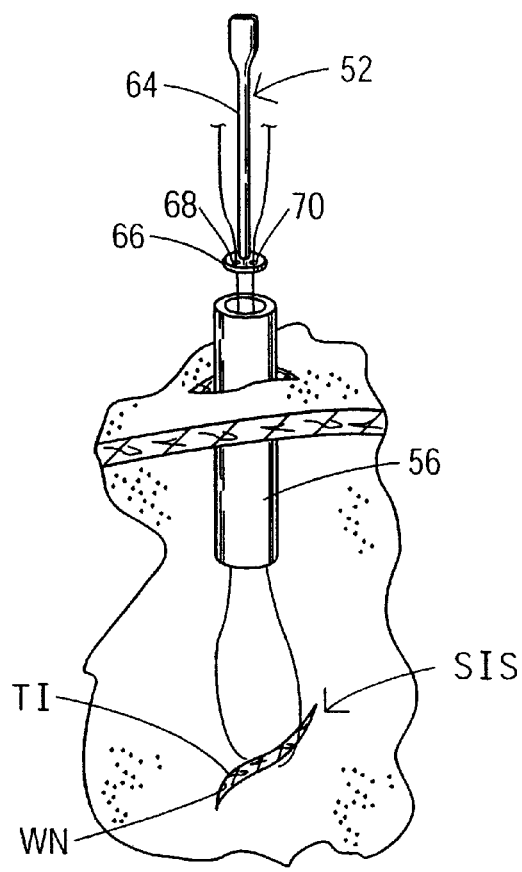
Figure 6D:
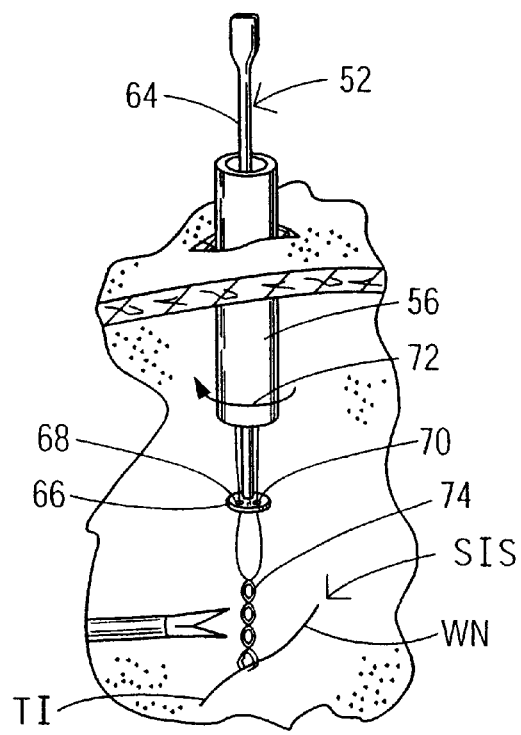

In a variation of the above procedure utilizing a different twisting instrument 52 (FIGS. 6C and 6D), a laparoscopic forceps 54 is partially inserted into an abdominal cavity ABC through a laparoscopic trocar sleeve or cannula 56, as shown in FIG. 6A. Jaws 58 at the distal end of forceps instrument 54 grip a suture needle 60 to which a suture or wire 62 is attached. Forceps 54 (or another forceps inserted through a different cannula) is manipulated to insert needle 60 through internal organic tissues TI at a surgical site SIS so that suture or wire 62 extends through the tissues and partially surrounds a wound or incision WN to be closed, as illustrated in FIG. 6B. Opposite ends of suture or wire 62 extend out of the patient through sleeve or cannula 56. Instrument 52 (FIG. 6C) is then used to entrain the opposite ends of suture or wire 62. More particularly, instrument 52 includes an elongate shaft 64 provided at one end with a flange 66 in turn formed with a pair of apertures 68 and 70 through which the ends of suture or wire 62 are passed, as shown in FIG. 6C. After the threading of the ends of suture or wire 62 through apertures 68 and 70, instrument 52 is inserted partially into the patient through sleeve or cannula 56, as illustrated in FIG. 6D. Then, instrument shaft 64 is rotated about its longitudinal axis, as indicated by an arrow 72 in FIG. 6D, to form a series of twists 74 in suture or wire 62 at wound or incision WN. The twists 74 are locked as described above with reference to FIGS. 3F, 4 and 5, and then severed by a scissors or cutter instrument 76.

Figure 7:
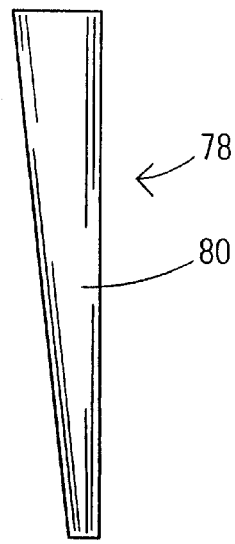
FIG. 7 is a schematic side elevational view of another laparoscopic or arthroscopic instrument in accordance with the present invention.
Figure 8:
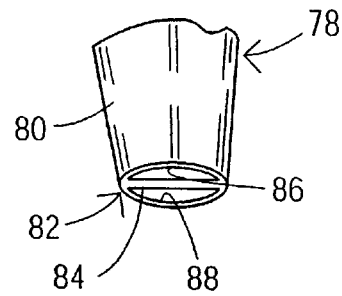
FIG. 8 is a partial perspective view of one end of the instrument of FIG. 7.
Figure 9:
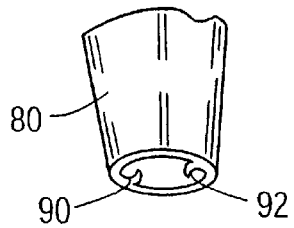
FIG. 9 is a partial perspective view similar to FIG. 8, showing a modified design for the instrument of FIG. 7.
Figure 10:
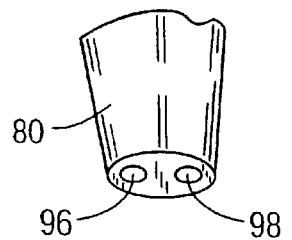
FIG. 10 is a partial perspective view similar to FIG. 8, showing a further alternative design for the instrument of FIG. 7.

FIG. 7 shows a twisting instrument 78 comprising a tube 80 which may have a slightly conical form. Tube 80 is open at opposite ends and is provided at a smaller end with a formation 82 (FIG. 8) for entraining two ends of a suture or wire. Formation 82 comprises a crosspiece 84 which divides the shaft opening into two portions 86 and 88. Alternatively, suture entrainment is accomplished by a pair of hooks 90 and 92, shown in FIG. 9, or a pair of eyelets 94 and 96, shown in FIG. 10.

Figure 11:
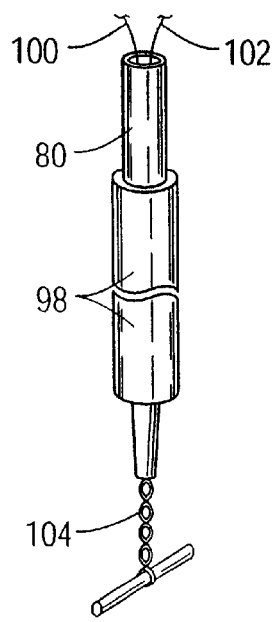
FIG. 11 is a schematic side elevational view showing the instrument of FIGS. 7 and 8, 9, or 10 inserted through a cannula to perform a laparoscopic or arthroscopic closure operation.

FIG. 11 illustrates the use of instrument 78. Tube 80, with opposite ends 100 and 102 of a suture or wire (not separately designated) entrained by formation 82 (FIG. 8), hooks 90 and 92 (FIG. 9), or eyelets 94 and 96 (FIG. 10), is inserted through a sleeve or cannula 98. Tube 80 is then rotated about its longitudinal axis to form a series of twists 104 in the suture or wire.

It is to be understood that the laparoscopic procedures detailed herein are merely exemplary of minimally invasive operations conducted under visual observation mediated by one or other type of endoscopic instrument.

What is claimed is:

1. A method for effecting a surgical closure, comprising:
   providing a medical instrument including a pair of jaws at a distal end;
   inserting a distal end portion of said instrument, including said jaws, into a patient;
   closing said jaws on internal tissues of the patient;
   threading an at least partially flexible elongate tie member from one of said jaws to the other of said jaws so that said tie member extends between said jaws about a portion of said internal tissues;
   opening said jaws and removing the jaws from said internal tissues, while maintaining said tie member extended about said portion of said internal tissues;
   after the opening of said jaws, rotating said jaws to twist said tie member about itself; and
   severing said tie member after the twisting thereof, to thereby form a closure at said internal tissues.

2. The method defined in claim 1 wherein said instrument is a laparoscopic instrument, the inserting of said distal end portion of said instrument into the patient including positioning a cannula in the patient and inserting said distal end portion of said instrument through said cannula.

3. The method defined in claim 1 wherein the threading of said tie member from said one of said jaws to said other of said jaws includes guiding said tie member along at least a portion of said one of said jaws, ejecting a distal tip of said tie member from said one of said jaws, and moving said distal tip from said one of said jaws to said other of said jaws.

4. The method defined in claim 1 wherein the rotating of said jaws includes turning at least a portion of said instrument including said jaws about a longitudinal axis of said instrument.

5. The method defined in claim 1 wherein the severing of said tie member includes inserting a cutting instrument into the patient and operating said cutting instrument to sever said tie member.

6. The method defined in claim 1, further comprising adding a drop of glue to the twisted tie member.

7. The method defined in claim 1, further comprising applying a clip or clamp to the twisted tie member.

8. A method for effecting a surgical closure, comprising:
   providing an elongate medical instrument;
   inserting a distal end portion of said instrument into a patient;
   introducing a distal end portion of an at least partially flexible elongate tie member through said instrument into the patient;
   applying said distal end portion of said tie member to internal tissues of the patient so that said distal end portion of said tie member extends around a portion of said internal tissues and so that a pair of tie member strands extend from said internal tissues;
   after the applying of said distal end portion of said tie member to said internal tissues, twisting said strands about one another;
   severing said tie member after the twisting of said strands, to thereby form a closure at said internal tissues.

9. The method defined in claim 8 wherein said instrument includes a pair of jaws at a distal end of said instrument, the applying of said distal end portion of said tie member to said internal tissues including threading said tie member from one of said jaws to the other of said jaws so that said tie member extends between said jaws about said portion of said internal tissues, further comprising opening said jaws and removing the jaws from said internal tissues, while maintaining said tie member extended about said portion of said internal tissues.

10. The method defined in claim 9 wherein the threading of said tie member from said one of said jaws to said other of said jaws includes guiding said tie member along at least a portion of said one of said jaws, ejecting a distal tip of said tie member from said one of said jaws, and moving said distal tip from said one of said jaws to said other of said jaws.

11. The method defined in claim 8 wherein the twisting of said strands includes rotating a portion of said instrument about a longitudinal axis to twist said strands about one another.

12. The method defined in claim 8 wherein said instrument is a laparoscopic instrument, the inserting of said distal end portion of said instrument into the patient including positioning a cannula in the patient and inserting said distal end portion of said instrument through said cannula.

13. The method defined in claim 8 wherein the severing of said tie member includes inserting a cutting instrument into the patient and operating said cutting instrument to sever said tie member.

14. The method defined in claim 8, further comprising adding a drop of glue to the twisted strands.

15. The method defined in claim 8, further comprising applying a clip or clamp to the twisted strands.

16. A method for effectuating a surgical closure, comprising:
   disposing a cannula in a patient so that said cannula traverses a skin surface of the patient and extends toward a surgical site inside the patient;
   inserting an at least partially flexible elongate tie member into the patient through said cannula;
   threading said tie member around internal tissues to be closed;
   inserting a distal end portion of a twisting tool into the patient so that said distal end portion extends to said surgical site, said twisting tool having at least one guide element for entraining said tie member; and after insertion of said distal end portion of said twisting tool into the patient and after threading of said tie member around internal tissues to be closed, rotating said twisting tool about an axis, thereby twisting said tie member at said surgical site.

17. The method defined in claim 16 wherein said twisting tool includes a pair of jaws at said distal end portion, the threading of said tie member including threading said tie member from one of said jaws to the other of said jaws so that said tie member extends between said jaws about said internal tissues to be closed, further comprising opening said jaws and removing the jaws from said internal tissues, while maintaining said tie member extended about said internal tissues to be closed.

* * * * *